United States Patent [19]

Huber

[11] Patent Number: 4,657,582
[45] Date of Patent: Apr. 14, 1987

[54] POLYHYDROXY POLYMER DELIVERY SYSTEMS

[75] Inventor: Ludwig K. Huber, Wayne, Pa.

[73] Assignee: Pennwalt Corporation, Philadelphia, Pa.

[21] Appl. No.: 739,264

[22] Filed: May 30, 1985

[51] Int. Cl.$^4$ ............................................. A01N 25/12
[52] U.S. Cl. ................... 71/121; 71/DIG. 1; 71/88; 71/117; 71/120; 71/118; 71/93; 424/22; 514/86; 514/89; 514/132; 514/141; 514/144
[58] Field of Search ................... 514/89, 86, 132, 141, 514/144; 424/19, 22; 71/DIG. 1, 118, 121; 252/316; 427/213.3, 213.31, 213.36; 264/4.7

[56] References Cited

U.S. PATENT DOCUMENTS

| | | | |
|---|---|---|---|
| 2,800,458 | 7/1957 | Green | 514/784 |
| 3,244,586 | 4/1966 | Rigterink | 514/89 |
| 3,565,818 | 2/1971 | Bayless et al. | 427/213.36 |
| 3,582,495 | 6/1971 | Emrick | 424/33 |
| 4,439,488 | 3/1984 | Trimnell et al. | 71/DIG. 1 |

FOREIGN PATENT DOCUMENTS 0873311  6/1971  Canada ........................ 71/DIG. 1
0081403  5/1982  Japan ............................. 71/120

OTHER PUBLICATIONS

Farm Chemicals Handbook 1976, p. D200 (Meister Publishing, 1976).
Shasha et al., "Starch-borate Complexes for EPTC Encapsulation," Chem. Abs. 100:134169d, (1984).

Primary Examiner—Glennon H. Hollrah
Assistant Examiner—Robert Lelkes

[57] ABSTRACT

A biologically active agent-containing composition is prepared by reacting an aqueous emulsion or dispersion of a suitable biologically active agent and an optional filler in an aqueous solution or gel of a polyhydroxy polymer and an inorganic salt, with a boric acid or boric acid derivative until an insolubilized matrix phase is formed having entrapped therein uniformly dispersed, discontinuous domains of said agent and an optional aqueous phase that can be separated from the matrix phase by decanting, filtration, or the like; the product is then dried and ground to the desired particle size. The composition is applied to the soil or plants where the biologically active agent is slow released for controlling pests.

16 Claims, No Drawings

POLYHYDROXY POLYMER DELIVERY SYSTEMS

BACKGROUND OF THE INVENTION

This invention relates to a method of preparing a composition for controlled release of active materials. More specifically, it relates to a method of preparing a polyhydroxy polymer/borate/salt composition with active materials contained within the matrix.

Polyhydroxy polymers such as polyvinyl alcohol (PVA) are known to react with borates to form water insoluble crosslinked polymers. Japanese Pat. No. 74/48073 describes the use of borax to harden PVA used in the form of micro-capsules to encapsulate perfume and flame retardants. South African Pat. Nos. 69/00122 and 69/00088 disclose the use of PVA-borate capsules for plasticizers and dyes. U.S. Pat. No. 4,110,431 discloses the use of polyvinyl alcohol-borate complexes formed by water activation of mixtures of the PVA and borax in situ for attaching plant treatment additives to plant foliage. U.S. Pat. No. 4,440,746 discloses that PVA can be converted into granular matrices with controlled release properties by reacting PVA/pesticide emulsions or dispersions with borates. Also, U.S. Pat. No. 4,439,488 discloses the reaction of starch or PVA pastes at alkaline pH with boric acid or boric acid derivatives to form an insolubilized gel matrix in which chemical biological agents such as pesticides can be entrapped for controlled release applications.

It is also known that polyhydroxy polymers such as polyvinyl alcohols can be coagulated from aqueous systems by the addition of various salts. French Pat. No. 1,304,891 describes a process for converting PVA into microcapsules by treating PVA/dye emulsions with inorganic sulfates.

SUMMARY OF THE INVENTION

The present invention is directed to a method of preparing a biologically active agent-containing composition comprising the steps of:

(a) preparing an aqueous emulsion or dispersion of a suitable biologically active agent and an optional filler in a matrix-forming material comprising an aqueous solution or gel of a polyhydroxy polymer (PHP), wherein said solution or gel has a solids concentration of said PHP of from about 3–40%, and where the relative amount of said PHP with respect to said biologically active agent is sufficient to entrap said agent within a matrix of said PHP, (b) blending into said emulsion or dispersion an inorganic salt for a sufficient time to distribute throughout the aqueous emulsion or dispersion, wherein the salt comprises 1–30% by weight of the product of step b, (c) reacting the product of b at an alkaline pH with boric acid or at an essentially neutral or alkaline pH with a boric acid derivative to form an insolubilized matrix phase having entrapped therein uniformly dispersed, discontinuous, domains of said agent and an optional aqueous phase that separates out from said matrix phase, and (d) recovering free-flowing particles of said entrapped biologically active agent.

Granular products prepared by this method are particularly useful for a prolonged delivery of pesticides by direct application to the soil or to plants.

DETAILED DESCRIPTION OF THE INVENTION

The active ingredient is emulsified or dispersed in the aqueous polyhydroxy polymer (PHP) system (solution, gel, or paste), the inorganic salt is added thereto, and the resulting mixture is thoroughly blended. The amount of PHP in this reactant mixture prior to addition of borate constitutes from about 3 to about 40% by weight of this reactant mixture, preferably from about 5 to about 30%. The amount of the inorganic salt in the reactant mixture is based on the weight of the reactant mixture prior to addition of borate and constitutes from about 1 to about 30% by weight of this reactant mixture, preferably from about 2 to about 20%. When the borate is added to the blended mixture, crosslinking (or complexing) of the PHP takes place. Either the borate can be added prior to the inorganic salt, the inorganic salt can be added before the borate, or both can be added simultaneously. Generally, it is preferred to add the borate last. In this way the formation of a hard-to-handle (viscous, sticky, voluminous if air gets entrapped) PHP borate gel is avoided or minimized, since the gel, as it is formed, breaks down into a harder, granular material. Depending on the type and concentration of PHP, filler, and inorganic salts used, some of the water will separate, thus resulting in a slurry. The free water can be removed mechanically (e.g., decantation, filtration, centrifugation), thus significantly reducing the drying time and expense. This is especially significant in cases where the active ingredient(s) is volatile or heat sensitive, or where the viscosity or solubility of the PHP requires the use of large amounts of water. The product is then freed from residual absorbed water by drying at ambient and/or elevated temperatures. If necessary, the dried product is ground and classified to the desired particle size. For argricultural applications, a particle size of about 14–60 mesh is used for granular formulations. For dusts, preferred particle range is 10–40 microns. If desired, various additives such as anticaking agents, masking agents, odorants, antidusting agents, colorants, etc., can be added at various stages of the process, in particular before, during, and after the grinding cycle.

A variety of water soluble/swellable polyhydroxy polymers can be used for the present invention. Included are various polyvinyl alcohols, starches (unmodified, modified and substituted types), dextrins, natural gums, cellulose derivatives, etc. Examples of the polyhydroxy polymers are the various partially or fully hydrolyzed polyvinyl acetates sold as polyvinyl alcohols (PVA) in various molecular weight ranges, corn or potato starch, oxidized starch, acid modified starch, hydroxyethyl starch, etc., or combinations thereof.

Inorganic salts useful in the invention include primarily water soluble sulfates such as various alkali and alkaline earth sulfates (Na, K, NH$_4$, Li, Mg, Ca), ferrous sulfate, various mono-, di- and tri-basic alkali phosphates, and combinations thereof, including various buffers, and alkali and alkaline earth chlorides, nitrates, carbonates, formates, and acetates. The salts can be used as solids or in solution. Obviously, also, combinations of acids (sulfuric, hydrochloric, phosphoric acid, etc.) with suitable bases (caustic, ammonia, etc.) can be employed.

Various sources of borate ions can be used. Suited materials are alkali metal, alkaline earth metal, and ammonium salts of borate anions such as tetraborate and metaborate anions. Examples are sodium borate (borax), sodium metaborate, ammonium pentaborate, and potassium borate. Also, combinations of boric acid and alkalizing agents are effective.

With respect to optional fillers, a large variety of powdered or granular materials can be employed. Examples are diatomites, attapulgites, bentonites, talcs, montmorillonites, perlites, vermiculites, corn cob grits, wood flour, lignin sulfonates, etc.

As far as the active ingredient(s) is concerned, a large variety of biologically active materials can be employed. In addition to the herbicides and insecticides, the matrices of the present invention will find general utility for the delivery of acaricides, fungicides, nematocides, bactericides, rodenticides, fumigants, animal repellents, insect repellents, plant growth regulators, fertilizers, pheromones, sex lures, flavors, odors, drugs, diet supplements, biological insect control agents, etc. Typical insecticides are, e.g., methyl parathion, parathion, ethoprop, fonofos, fenitrothion, chlorpyrifos, diazinon, phorate, etc., which can be used undiluted, in the form of suited solutions or emulsifiable concentrates, on fillers or salts, or in combinations. Typical herbicides include trifluralin, endothall, 2,4-D, monuron, alachlor, metalachlor, atrazine, and metribuzin.

The type of biologically active agent that might be delivered from one of these matrices is limited only by its compatibility with the system. For example, it should not be decomposed by the process or react in such a way as to prevent matrix formation, or be irreversibly bound to the polymer. The combination of water solubility and polymer/filler compatibility should be such that the active agent should not be substantially lost in the aqueous phase.

The amounts of the various ingredients by weight in the final formulation can vary widely, and range from about 5-90% of the PHP(s), 1-50% of the active ingredient(s), 0-80% of the filler(s), 2-40% of the inorganic salts, and 1-25% of the borates. Preferred ranges are: 10-70% for PHP, 5-40% for active ingredients, 5-60% for fillers, 2-30% for inorganic salts, and 1-15% for borates. The exact amounts of inorganic salts and borates required for optimal performance vary with the type and amount of the other ingredients and are best determined experimentally.

In the following examples all percentages are by weight unless otherwise stated.

EXAMPLE 1

Five grams of Gelvatol 9000 (a partially hydrolyzed PVA marketed by Monsanto Corp., percentage of hydrolysis 85 to 88%, medium viscosity) were dissolved in 45 grams of water. To this solution 19.0 grams of methyl parathion-loaded diatomite powder [prepared by soaking 14.5 grams of Celatom MN-39 (Eagle Picher) with 4.5 grams of technical methyl parathion in ~40 ml methylene chloride, and removing volatile components at ~50° C./130 mm Hg] were added. Then, 9.0 grams of 25% $Na_2SO_4$ solution were added dropwise with stirring, followed by dropwise addition of 5.6 grams of 10% warm borax solution. The resulting mixture was filtered and the filter cake (42.8 grams of crumbs) was dried overnight at ambient temperature. The essentially dry product (24.4 grams) was further dried for 2½ hours at ~75° C. and the resulting material (24.0 grams) was ground in a blender and classified to a 14-40 mesh size. The material contained 13.0% of methyl parathion.

For comparison, in an experiment similar to the above, 19.0 grams of methyl parathion-loaded diatomite powder (prepared as described above) were dispersed in 50 grams of 10% aqueous Gelvatol 9000 solution. Upon addition of 5.0 grams of 10% warm borax solution, a rubbery solid lump was formed which retained all the water and was hard to mix. The product was cut into smaller pieces with a knife and dried overnight at ambient temperature. The product (35.7 grams of lumps which were still wet at the bottom) was further dried for 2½ hours at ~75° C., and the resulting material (23.4 grams) was ground in a blender and classified to a 14-40 mesh size. The granulate analyzed for 13.2% of methyl parathion. When, prior to drying, 2.25 grams of $Na_2SO_4$ are added to a portion of the above mentioned rubbery material with thorough mixing, the rubbery mass breaks up into a granulate and free water. This mixture is filtered and worked up as mentioned above.

EXAMPLE 2

Fifty grams of 10% aqueous Gelvatol 9000 solution and 19.0 grams of methyl parathion-loaded diatomite were combined as in Example 1. Then, 7.2 grams of 5% aqueous $H_3BO_3$ solution were added with stirring, followed by 9.0 grams of 25% $Na_2SO_4$ solution. The resulting somewhat creamy mixture was then neutralized by dropwise addition of 14.0 grams of 20% aqueous $Na_2HPO_4$ solution. The resulting mixture was filtered and the filter cake (43.0 grams) was dried overnight at ambient temperature and then for 2½ hours at ~75° C. The dried product (24.5 grams) was ground in a blender and classified to a 14-40 mesh size. It analyzed for 12.7% of active ingredient.

EXAMPLE 3

Nineteen grams of methyl parathion-loaded diatomite powder (prepared by dropwise addition of 9.25 grams of technical methyl prathion to 9.75 grams stirred Celatom MN-39) were blended with 25 grams of a 10% aqueous solution of Vinol 205 (a partially hydrolyzed PVA marketed by Air Products, percentage of hydrolysis 87 to 89%, low viscosity). Then 4.5 grams of 25% aqueous $Na_2SO_4$ solution were added with stirring, followed by dropwise addition of 2.8 grams of 10% warm borax solution. After stirring for ½ hour with repeated mixing, the mixture was filtered and the filter cake (34.8 grams) was dried overnight at ambient temperature and then for 2½ hours at ~75° C. The resulting product (20.5 grams) was ground in a blender and classified to a 14-40 mesh size. It contained 31.9% of active ingredient.

EXAMPLE 4

Nineteen grams of diazinon-loaded diatomite [prepared by dropwise addition of 4.5 grams of technical diazinon to 14.5 grams stirred Celatom MP-78 (Eagle Picher)] were blended with 25 grams of 10% aqueous solution of Vinol 205. Then, 4.8 grams of 25% aqueous $Na_2SO_4$ solution were added with mixing, followed by dropwise addition of 2.9 grams of 10% warm borax solution. After sitting for 2 hours with occasional mixing, the mixture was filtered and worked up as usual. The resulting 14-40 mesh granulate analyzed for 16.2% of diazinon.

EXAMPLE 5

Nineteen grams of chlorpyrifos-loaded calcium sulfate powder [prepared by soaking 15.4 grams of Snow White Filler (United States Gypsum Company) with 3.6 grams of technical chlorpyrifos in about 40 ml methylene chloride and removing volatiles at ~50° C./130 mm Hg] were blended with 35 grams of a 14.3% aqueous solution of Vinol 205. Then 6.5 grams of 25% aqueous $Na_2SO_4$ solution were added dropwise with mixing, followed by dropwise addition of 5.6 grams of 10% warm borax solution. After sitting for about 1 hour with occasional blending, the mixture was filtered and worked up as usual. The 14–40 granulate thus obtained contained 15.1% of active ingredient.

EXAMPLE 6

Nineteen grams of dyfonate-loaded talc [prepared by adding dropwise 3.8 grams of technical dyfonate to 15.2 grams stirred talc (Nytal 400, marketed by R. T. Vanderbilt Company)] were blended with 50 grams of a 10% aqueous solution of Vinol 205. Then 9.0 grams of 25% aqueous $Na_2SO_4$ solution were added dropwise with stirring, followed by addition of 5.6 grams of 10% warm borax solution. After sitting for about ½ hour, the liquid was removed by filtration and the product worked up as usual. The resulting 14–40 mesh granulate analyzed for 13.0% of dyfonate.

EXAMPLE 7

An emulsion of 6.4 grams of Mocap EC (marketed by Rhone Poulenc) in 14.5 grams of a 17.2% aqueous solution of Vinol 205 was mixed with 12.6 grams Celatom MP-78. After soaking for ½ hour, the wet granulate was blended with 3.0 grams of 25% aqueous $Na_2SO_4$ solution and then with 3.7 grams of 10% warm borax solution. After sitting for 2 hours with occasional mixing, the product was dried directly and worked up in the usual way. The resulting 14–40 mesh granulate assayed for 19.6% of ethoprop.

EXAMPLE 8

A mixture of 13.5 grams of corn starch (Starch 3005, marketed by Corn Products), 21.5 grams of water, and 3.1 grams of technical trifluralin was blended in a Waring Blender while 15 ml of 6.6% aqueous NaOH solution were added dropwise. The starch gelatinized and as the mixture became warmer trifluralin melted and became well dispersed. The mixture was allowed to cool to about 35° C., and then 6.0 grams of anhydrous $Na_2SO_4$ were added incrementally with stirring. Subsequently, 1.5 grams of finely ground $H_3BO_3$ were added incrementally with continued blending whereby the crumb-like product became increasingly harder and finer. The wet mixture was filtered and the filter cake (34.0 grams hard granulate) was dried overnight at ambient temperature. The resulting granulate (21.3 grams) was classified directly to yield 9.4 grams of the desired 14–40 mesh particle range. Grinding the coarse residue once for about 15 seconds in a blender brought the amount of 14–40 mesh granulate to a total of 14.8 grams. The product analyzed for 12.1% of active ingredient.

In an experiment similar to the one mentioned above, the order of adding the anhydrous sodium sulfate and boric acid was reversed; 1.5 grams of boric acid were reacted with the mixture of the corn starch, water, trifluralin and sodium hydroxide; then 8 grams of the anhydrous sodium sulfate were thoroughly mixed into the reaction product. Again, a wet granulate was formed which could be easily filtered. The filter cake (33.8 grams of hard granulate) was dried overnight at ambient temperature. The resulting dry granulate (21.2 grams) was classified directly to yield 11.4 grams of the desired 14–40 mesh particle range.

In an experiment similar to the above but omitting the sodium sulfate [as described by D. Trimnell et al., J. Appl. Pol. Sci. 27, 3919–28, (1982)] and herein incorporated by reference, a rather sticky and rubbery cluster-type of product was obtained which, even upon the recommended addition of 1.8 grams of solid starch powder retained a strong tendency to stick and fuse together to large clusters. The product was dried overnight at ambient temperature and the resulting 20.8 grams of chunks sieved. Essentially, no product passed a 14 mesh sieve.

The material was ground in a blender for about 15 seconds and sieved. After 9 grinding/sieving cycles the total of 14'40 mesh granulate amounted to 11.5 grams.

EXAMPLE 9

A mixture of 13.5 grams of corn starch, 21.0 grams of water, and 3.1 grams of technical trifluralin was blended in a Waring Blender while 15 ml of 6.6% aqueous NaOH solution were added dropwise. A well dispersed mixture formed as a result of gelatinization of the starch and melting of trifluralin. The mixture was allowed to cool to about 30° C. Then, 6.0 grams of $MgSO_4$ were added incrementally with stirring, followed by incremental addition of 1.5 grams of finely ground $H_3BO_3$. Slightly rubbery non-sticky crumbs were formed which were filtered and the resulting filter cake (32.0 grams crumbs) was dried overnight at ambient temperature. The dried granulate (20.9 grams) was ground and classified (2 passes) to yield 15.1 grams product of 14–40 mesh particle size. The product assayed for 13.2% of active ingredient.

EXAMPLE 10

A mixture of 16.5 grams of methyl parathion-loaded diatomite (prepared by dropwise addition of 4.6 grams of technical methyl parathion to 11.9 grams stirred Celatom MP-78) and 21.8 grams of 10% aqueous solution of Vinol 205 was allowed to soak for about 15 minutes. Then, 1.0 gram of finely powdered magnesium sulfate was added with stirring and the mixture soaked for 15 minutes with repeated blending. Then, 3.35 grams of 10% warm borax solution were added incrementally with stirring. An essentially granular wet mixture was formed. After sitting for several hours with occasional mixing, the liquid portion of the reaction mixture was drained. The residue was dried overnight at ambient temperature and finally for 2½ hours at ~70° C. The yield was 18.7 grams of granulate/crumbs.

In a series of similar experiments other additives were substituted for the above magnesium sulfate to effect formation of essentially granular reaction mixtures and/or formation of free water which was removed by simple draining. The results are tabulated in Table I as follows:

TABLE I

| Salt | Amount Used (g) | 10% Borax Used (g) | Dried Reaction Prod. (g) | Drained Water (g) |
|---|---|---|---|---|
| $MgSO_4$ | 1.0 | 3.4 | 18.7 | 6.9 |
| Ca Sulfate[a] | 1.0 | 3.4 | 18.9 | 1.3 |
| Ca Sulfate[b] | 1.0 | 3.4 | 19.2 | 1.0 |
| $Al_2(SO_4)_3 \cdot 18H_2O$ | 0.9 | 15.3 | 18.8 | 13.0 |
| $(NH_4)_2HPO_4$ | 1.0 | 3.4 | 18.9 | 2.5 |

TABLE I-continued

| Salt | Amount Used (g) | 10% Borax Used (g) | Dried Reaction Prod. (g) | Drained Water (g) |
|---|---|---|---|---|
| NaH$_2$PO$_4$.2H$_2$O/Na$_2$HPO$_4$ | 0.7 + 1.0 | 4.5 | 19.7 | 3.1 |
| Na$_2$HPO$_4$/Na$_3$PO$_4$.12H$_2$O | 0.5 + 1.2 | 3.4 | 19.4 | 1.0 |
| Ca(H$_2$PO$_4$)$_2$ | 1.0 | 15.0 | 19.3 | 11.0 |
| NaCl | 1.0 | 3.4 | 18.7 | 4.9 |
| KCl | 1.0 | 3.4 | 18.7 | 3.8 |
| CaCl$_2$ | 1.0 | 4.4 | 19.6 | 0 |
| NaNO$_3$ | 2.0 | 3.4 | 19.4 | 4.4 |
| NH$_4$NO$_3$ | 1.0 | 5.0 | 18.9 | 4.3 |
| NaHCO$_3$ | 1.0 | 3.4 | 18.7 | 1.2 |
| Ca Carbonate[c] | 2.0 | 4.4[d] | 10.0 | 0 |
| Na Formate | 1.0 | 3.4 | 18.6 | 6.5 |
| Na Acetate.3H$_2$O | 1.6 | 3.4 | 18.5 | 5.7 |

[a]Snowwhite (U.S Gypsum)
[b]Molding Plaster (U.S. Gypsum)
[c]Albacar (Pfizer)
[d]Mixture became granular after 1½ days.

EXAMPLE 11

Thirty-three grams of methyl parathion-loaded diatomite [prepared by dropwise addition of 9.2 grams of technical methyl parathion to 23.8 grams stirred Celatom MP-78 (Eagle Picher)] were soaked for about 15 minutes in 43.6 grams of a 10% aqueous solution of Vinol 205. Then 7.95 grams of 25% aqueous solution of sodium sulfate were added dropwise with stirring. After soaking for about 15 minutes, 6.7 grams of 10% warm borax solution were added incrementally with stirring. An essentially granular wet mixture was formed. After sitting for two hours with occasional blending, the mixture was drained and the solids dried overnight at ambient temperature (41.5 grams) and finally for 2½ hours at ~70° C. Most of the resulting crumbs/granulate (37.6 grams) could be pushed through a 14 mesh sieve. The product was resieved, the coarse portion ground in a blender, and the product classified to yield 31.4 grams of a 14–40 mesh granulate.

In an experiment similar to the above but substituting 1.95 grams of finely ground potassium sulfate for the sodium sulfate solution, 30.1 grams of a 14–40 mesh granulate were obtained.

In an experiment similar to the above but substituting 7.9 grams of 25% aqueous ammonium sulfate solution for the sodium sulfate solution, 30.1 grams of a 14–40 mesh granulate were obtained.

For comparison, in an experiment similar to the above a mixture of 33 grams of methyl parathion-loaded Celatom MP-78 in 43.6 grams of a 10% aqueous solution of Vinol 205 was treated with 6.7 grams of a 10% warm aqueous borax solution. A rubbery solid lump was formed which was repeatedly cut into small pieces with a knife to achieve some mixing. On sitting, the pieces fused together without separation of water and/or formation of a granulate. After sitting for two hours with repeated cutting/mixing, the product was cut again and spread for drying similar to the above products. After drying overnight at ambient temperature, it weighed 53.8 grams; after drying for an additional 24 hours it weighed 36.1 grams. The product was finally dried for 2½ hours at ~70° C. to yield 35.4 grams of lumps, which could not be pushed through a 14 mesh sieve in a fashion similar to the above products. Grinding in a blender and classification yielded 23.2 grams of a 14–40 mesh granulate.

EXAMPLE 12

Nineteen grams of methyl parathion-loaded diatomite powder (prepared as described in Example 1) were dispersed in 50 grams of 10% aqueous solution of Vinol 107 (a fully hydrolyzed PVA marketed by Air Products, 98 to 99% hydrolyzed, low viscosity). Then 9.0 grams of 25% aqueous Na$_2$SO$_4$ solution were added dropwise with stirring, followed by dropwise addition of 17.5 grams of 10% warm borax solution. The resulting mixture was filtered and the filter cake (47.9 grams of crumbs) was dried overnight at ambient temperature and finally for 2½ hours at ~75° C. The resulting material (24.4 grams) was ground in a blender and classified to a 14–40 mesh size. It contained 13.2% methyl parathion.

In an experiment similar to the above, 50 grams of 10% aqueous solution of Vinol 350 (a fully hydrolyzed PVA marketed by Air Products, 98 to 98.8% hydrolyzed, high viscosity) were substituted for the Vinol 107 solution. The resulting granular material contained 12.6% methyl parathion.

In another experiment, 50 grams of 10% aqueous solution of Gelvatol 40–20 (a partially hydrolyzed PVA marketed by Monsanto Corp., 73 to 77% hydrolyzed, very low viscosity) were substituted for the Vinol 107 solution. The resulting granular material contained 11.9% methyl parathion.

In another experiment, 16.5 grams of methyl parathion-loaded diatomite (prepared from 4.6 grams of technical methyl parathion and 11.9 grams of Celatom MP-78) in 21.9 grams of 10% aqueous solution of Vinol 125 (a super-hydrolyzed PVA marketed by Air Products, 99.6% hydrolyzed, medium viscosity) were treated with 4.0 grams of 25% aqueous Na$_2$SO$_4$ solution, followed by 3.35 grams of 10% warm borax solution. The resulting slightly wet granulate was dried and classified to obtain a 14–40 mesh granulate.

EXAMPLE 13

Twenty grams of an aqueous gel prepared from 4.0 grams of Clineo 716D (a hydroxyethylated starch marketed by Clinton Corn Processing Co.) and 16 grams water were heated with 0.4 grams of technical trifluralin with stirring until a uniform orange mixture was formed. Then with continued stirring, 5.0 grams of sodium sulfate were added incrementally at ambient temperature, followed by dropwise addition of 2.5 grams of 10% warm aqueous borax solution. The mixture became more compact/granular. After sitting for several hours with occasional blending, the mixture was filtered to yield 10.2 grams of amber crumbs. The product was dried overnight at ambient temperature and the dry crumbs (5.8 grams) were ground in a blender and classified to form 4.4 grams of a granulate of 14–40 mesh range corresponding to 76% of total product.

In an experiment similar to the above, but conducted in the absence of sodium sulfate, no separation of water took place.

In an experiment similar to the above 0.4 grams of technical trifluralin in 20 grams of a 20% aqueous gel of Clineo 716D were treated with 5.0 grams of sodium sulfate alone. After sitting for several hours with occasional additional blending, the mixture was filtered to yield 13.85 grams of yellow coarse powder. The product was dried overnight at ambient temperature and the light and rather soft powder/granulate (7.15 grams) was dried for additional 24 hours. The resulting product (7.05 grams) was sieved and classified to form 4.0 grams of a rather soft granulate of 14–40 mesh range, corresponding to 56% of total product.

In another experiment similar to the above sodium sulfate/borax procedure, 4.0 grams of Clinsize 756B (a cyanoethylated starch marketed by Clinton Corn Processing Co.) were substituted for the Clineo 756B to yield 5.8 grams of trifluralin containing product.

EXAMPLE 14

Nineteen grams of methyl parathion-loaded diatomite powder (prepared as described in Example 1) were combined with 50 grams of 10% aqueous Gelvatol 9000 solution. Then 12.0 grams of 25% aqueous $Na_2SO_4$ solution were added dropwise with stirring, followed by dropwise addition of 12.9 grams of 20% sodium metaborate solution. The mixture was filtered and the filter cake (57.3 grams of fine crumbs) was dried overnight at ambient temperature and finally for 2½ hours at ~75° C. The resulting granulate (25.7 grams) was ground in a blender and classified to a 14–40 mesh size. It analyzed for 12.9% of active ingredient.

EXAMPLE 15

The granular product of Example 3 was tested in a laboratory soil bioassay using three-day old housefly larvae as test organisms. The soil was treated with the granular product, thereafter twenty-five larvae were exposed to the treated soil at intervals of 3, 31, 45 and 59 days; the number of adult flies emerging from the soil was counted. The granular product was used at a rate equivalent to ½ lb. of active ingredient per acre applied in 6" bands spaced 40" apart. The results were recorded in Table II. Percent killed is the percent reduction in adult houseflies emerging from the soil. For comparison, a commercial granular soil insecticide (sold under the trademark Lorsban 15G) was included. A control experiment was also run where the soil was not treated with any pesticide.

TABLE II

| | % Killed | | | |
|---|---|---|---|---|
| Days | 3 | 31 | 45 | 59 |
| Example 3 | 35 | 93 | 93 | 87 |
| Lorsban 15G | 87 | 72 | 46 | 29 |
| Control | 5 | 1 | 0 | 5 |

EXAMPLE 16

The granular product of Example 5 was tested by the method described in Example 15. The results are recorded in Table III. For comparison a commercial insecticide (marketed under the trademark Lorsban 15G) was included.

TABLE III

| | % Killed | | | |
|---|---|---|---|---|
| Days | 3 | 31 | 45 | 59 |
| Example 5 | 57 | 93 | 65 | 36 |
| Lorsban 15G | 74 | 43 | 23 | 13 |
| Control | 0 | 0 | 20 | 7 |

EXAMPLE 17

The granular product of Example 6 was tested by the method described in Example 15. The results are recorded in Table IV. For comparison a commercial granular soil insecticide (sold under the trademark Dyfonate 20G) was included.

TABLE IV

| | % Killed | | | |
|---|---|---|---|---|
| Days | 3 | 31 | 45 | 59 |
| Example 6 | 97 | 99 | 98 | 95 |
| Dyfonate 20G | 100 | 100 | 97 | 77 |
| Control | 2 | 9 | 14 | 2 |

What is claimed:

1. A method of preparing a slow release, pest control agent-containing composition consisting essentially of the steps of:
   (a) preparing an aqueous emulsion or dispersion of suitable pest control agent and an optional filler in a matrix-forming material comprising an aqueous solution or gel of a polyhydroxy polymer (PHP) selected from the group of polyvinyl alcohols and starches, wherein said solution or gel has a solids concentration of said PHP of from about 3–40%, and wherein the relative amount of said PHP with respect to said pest control agent is sufficient to entrap said agent within a matrix of said PHP,
   (b) blending into said emulsion or dispersion a salt selected from the group consisting of ammonium, alkali and alkaline earth sulfates, phosphates, chlorides, carbonates, nitrates, formates, and acetates for a sufficient time to distribute throughout the aqueous emulsion or dispersion, wherein the salt comprises 1–30% by weight of the product of step b,
   (c) reacting the product of b at an alkaline pH with boric acid or at an essentially neutral or alkaline pH with an inorganic boric acid derivative to form an insolubilized matrix phase having entrapped therein uniformly dispersed, discontinuous domains of said agent and an optional aqueous phase that separates out from said matrix phase, and
   (d) recovering free-flowing particles of said entrapped pest control agent.

2. The method of claim 1 where steps b and c are performed in reverse order or simultaneously.

3. The method of claim 1 wherein the pest control agent is selected from the group consisting of herbicides, insecticides, acaricides, fungicides, nematocides, bactericides, rodenticides, fumigants, animal repellants, insect repellants, pheromones, sex lures, and biological insect control agents.

4. The method of claim 3 wherein the pest control agent is on a filler, or a filler is blended in the PHP mixture simultaneously with step b or directly after step b but before step c.

5. The method of claim 3 wherein the recovery step of the free-flowing particles comprises decanting, filtering or centrifuging the reaction product mass, drying the product mass, and, if necessary, grinding the dried product to the desired particle size.

6. The method of claim 3 wherein the recovery step of the free-flowing particles comprises drying the product mass and, if necessary, grinding the dried product to the desired particle size.

7. The method of claim 5 or 6 wherein the PHP is a polyvinyl alcohol.

8. The method of claim 7 wherein the salt is sodium sulfate.

9. The method of claim 8 wherein the pest control agent is parathion- or methyl parathion.

10. The method of claim 8 wherein the pest control agent is diazinon.

11. The method of claim 8 wherein the pest control agent is chlorpyrifos.

12. The method of claim 8 wherein the pest control agent is fonofos.

13. The method of claim 8 wherein the pest control agent is ethoprop.

14. The method of claim 5 or 6 wherein the PHP is a starch.

15. The method of claim 4 wherein the salt is sodium sulfate.

16. The method of claim 15 wherein the pest control agent is trifluralin.

* * * * *